(12) United States Patent
Milo

(10) Patent No.: US 6,206,911 B1
(45) Date of Patent: Mar. 27, 2001

(54) STENT COMBINATION

(76) Inventor: Simcha Milo, 6a Noga Street, Haifa, 33407 (IL)

(*) Notice: Subject to any disclaimer, the term of this patent is extended or adjusted under 35 U.S.C. 154(b) by 0 days.

(21) Appl. No.: 09/180,092

(22) PCT Filed: Nov. 17, 1997

(86) PCT No.: PCT/IB97/01574
§ 371 Date: Nov. 2, 1998
§ 102(e) Date: Nov. 2, 1998

(87) PCT Pub. No.: WO98/26732
PCT Pub. Date: Jun. 25, 1998

Related U.S. Application Data

(60) Provisional application No. 60/034,787, filed on Dec. 19, 1996.

(51) Int. Cl.$^7$ .................................................. A61F 2/06
(52) U.S. Cl. ........................................ 623/1.15; 623/1.17
(58) Field of Search ................................. 623/1, 12, 1.15, 623/1.17, 1.36; 606/194

(56) References Cited

U.S. PATENT DOCUMENTS

| | | | |
|---|---|---|---|
| 5,556,414 | * 9/1996 | Turi | 623/1.11 |
| 5,667,523 | * 9/1997 | Bynon et al. | 623/12 X |
| 5,681,345 | * 10/1997 | Euteneuer | 623/12 X |
| 5,695,516 | * 12/1997 | Fischell et al. | 606/194 |
| 5,800,526 | * 9/1998 | Anderson et al. | 623/1 |
| 5,807,404 | * 9/1998 | Richter | 623/1 |
| 5,824,037 | * 10/1998 | Fogarty et al. | 623/1 |
| 5,843,164 | * 12/1998 | Frantzen et al. | 623/1 |
| 5,871,535 | * 2/1999 | Wolff et al. | 623/1 |
| 5,931,867 | * 8/1999 | Haindl | 606/151 X |

* cited by examiner

Primary Examiner—David H. Willse
Assistant Examiner—Brian E. Pellegrino
(74) Attorney, Agent, or Firm—Arnall Golden & Gregory, LLP

(57) ABSTRACT

Radially expandable intraluminal stents (11) suitable for providing interior support within a human blood vessel are disclosed. A material (33') used to construct the stent (11) is formed into diamond cells (35). The diamond cells (35) each have arms (37) of equal length. Diamond cells (35) are interconnected to other diamond cells (25) by legs (39, 39a) or to pairs of smaller cells (41) which have a common vertex and four arms (43) of equal length. Needle-like prongs (51, 53) are attached to the diamond cells (35) at their vertex to function as attachment means for a biological membrane (57').

15 Claims, 3 Drawing Sheets

STENT COMBINATION

This application claims priority from U.S. provisional application Ser. No. 60/034,787, filed Dec. 19, 1996. The disclosure of this application is incorporated herein by reference.

This invention relates to vascular stents and the like and more particularly to intraluminal stents and to such stent and biomembrane combinations which can be carried to a desired in vivo location and then expanded, as by use of a balloon catheter, into an operative configuration. Reference is made to Disclosure Document No. 404,393 which was filed on Sep. 9, 1996.

BACKGROUND OF THE INVENTION

Expandable stents have now proved to be extremely useful in treating occluded blood vessels and/or diseased blood vessels. Whereas there are numerous expandable stents that are now commercially available, these stents invariably undergo a foreshortening in axial length as a result of their radial expansion. When treating a diseased blood vessel, and oftentimes when treating an occluded blood vessel, such as a coronary artery or other peripheral vessel, there is a desire to carry a tubular graft in surrounding relationship to the stent in order to deliver the graft with the stent to patch a diseased vascular location affected with lesions or the like. It is believed such grafts may prevent intimal cell proliferation caused by direct contact of a metal stent with the vessel wall which frequently otherwise results in early stent occlusion. Heretofore, truly acceptable techniques have not been developed for carrying such grafts to a desired location in surrounding relationship to a stent on a balloon catheter or the like. Because such present commercially available stents undergo axial foreshortening as a result of expansion, tubular grafts secured to the exterior of such a stent would be likewise subject to such foreshortening and would undergo undesirable wrinkling even if they were slightly elastic.

SUMMARY OF THE PRESENT INVENTION

The present invention provides multiple designs of expandable stents which are created so as to undergo essentially no axial foreshortening (or only minimal axial foreshortening) when expanded from an unexpanded or compressed configuration to an operative configuration. Moreover, tubular biological membranes can now be effectively interconnected with expandable stents of this character and effectively located in surrounding, isolating relationship to the stent. Interconnection may be via pairs of needle-like projections or prongs which may be bent to have a radial orientation during the installation of such a tubular biomembrane upon the unexpanded stent and then bent in opposite directions back into the plane of the stent, preferably in opposite axially extending directions, to secure the tubular biomembrane in such a mating connection.

DESCRIPTION OF THE PREFERRED EMBODIMENTS

The stents of the invention are provided with properties which render them superior to commercially available expandable intraluminal stents. The stents illustrated herein not only experience substantially no shortening in axial length upon expansion but also demonstrate high lateral pliability, allowing the stent to relatively easily follow the curved features of a blood vessel or the like as it is being inserted on a balloon catheter or the like. Both of these objectives are achieved while at the same time providing good radial support, sufficient to withstand the tendency of a blood vessel that has been ballooned to recoil to a smaller diameter. Such radial support remains a characteristic even though the stent may have been radially expanded to increase its unexpanded or crimped diameter by a factor of about 2 to 4, e.g. from a crimped exterior diameter of about 1.3–1.5 mm or even as low as 1.1 mm.

In addition, the stents of the invention can be advantageously employed in combination with tubular, biological membranes, sometimes referred to as biomembranes, which will serve to separate the major portion of the metal material of the stent from the vascular wall and thus obviate reocclusion secondary to intimal cell proliferation. Biomembranes can also be valuable in repairing blood vessels in certain diseased states, as for example those which are torn or have suffered the results of affection with different lesions or the like. Impregnation of the exterior surface and the interior surface of biomembranes with different pharmaceuticals can be effectively used to differentially deliver medications. These stent biomembrane combinations can be carried to the desired location in a patient upon a balloon catheter and then expanded to just the desired diameter by the careful expansion of the balloon catheter. As a result, these stents have a substantial advantage in flexibility of usage over self-expanding stents which may inherently continue to expand past the desired diameter, resulting in their becoming undesirably deeply embedded in the vessel wall. Because the stents of the present invention do not significantly decrease in axial length upon expansion, they are perfectly suited for use in combination with biological membranes which are pliable and slightly stretchable and elastic.

Figure 1:
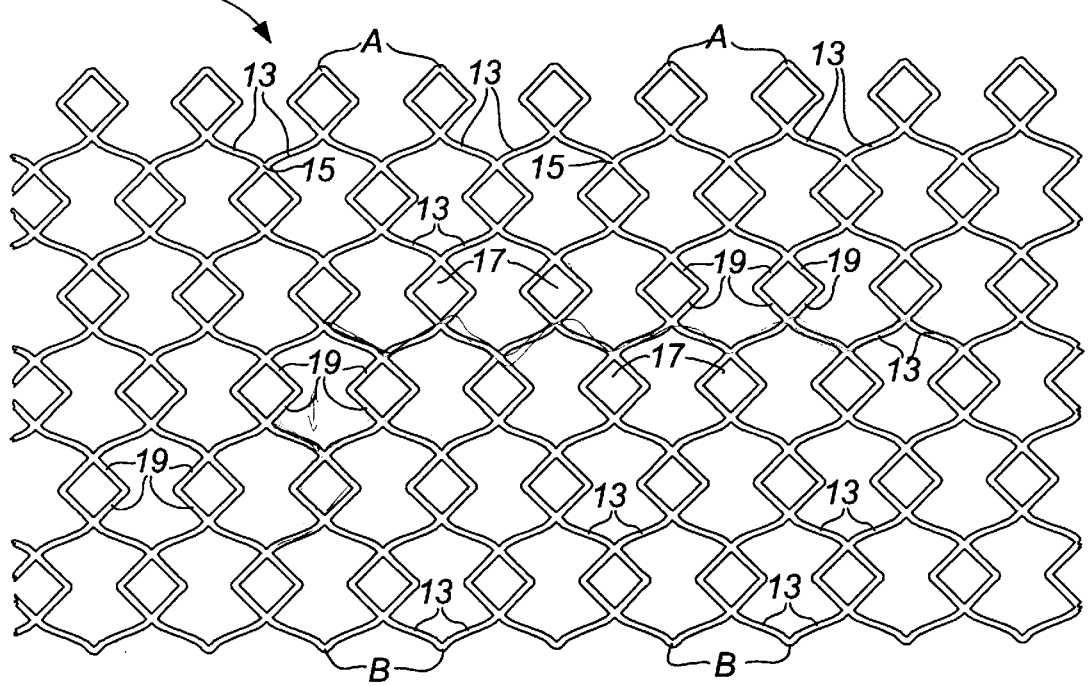
FIG. 1 is a plan view of an expanded form of stent material before it is rolled and welded into a tubular stent and then appropriately crimped, which material design is effective to create a particularly advantageous crimped stent.

Illustrated in FIG. 1 is a generally rectangular piece or blank of malleable metal sheet 11 which represents an expanded framework of an approximate shape for being rolled, welded (or otherwise joined) and crimped to create a balloon-expandable stent. By malleable is meant a non-brittle, pliable metal that can be bent to a different shape but which has sufficient stability so as to retain its expanded shape when subjected to the normal forces that may likely be encountered within the human body. The illustrated stent blank 11 is constructed with an open framework which includes a plurality of axially extending legs which have a zig-zag configuration and which are formed by interconnected leg segments 13. Each junction between adjacent legs in the framework is also the vertex of a diamond-shaped cell 17. Each of the cells 17 is made up of four interconnected arms 19, and thus the cells 19 serve as spacers which uniformly space apart the adjacent, axially-extending, zig-zag legs. Viewed from a different perspective, the open framework material has a construction in the form of side-by-side axially extending rows of major diamond-shaped cells with the adjacent rows being staggered so as to interfit and create a regular pattern. The result of such overlapping is that each of these major cells would include two spaced-apart minor diamond cells 17 along with pairs of flanking leg segments 13.

The stent material may be made from flat wire that is welded or suitably joined at the points of contact; however, it is preferably made by suitably machining a sheet of malleable metal, such as titanium, stainless steel or other suitable metal alloy material. Wire or sheets of a memory-type nickel alloy, such as Nitinol, might also be used. Such could be shaped and then welded to create a tubular structure of desired diameter and length, and such a tubular structure might then be cooled below the temperature transformation level and suitably compressed before being loaded into a catheter.

When a sheet of nonmemory malleable metal is used, suitable openings are formed in such a sheet by conventional laser-cutting techniques or by electrical discharge machining or the like. Such an open framework may alternatively be machined from a thin metal tube, seamless or welded, although more sophisticated equipment might be required to machine a tubular body. Thus, stents may be preferably made from a flat sheet, as depicted in FIG. 1, which is subsequently rolled into a tubular configuration (which would be about a horizontal axis as oriented in FIG. 1) and then welded or otherwise appropriately fusion-bonded. For example, it may be made from a sheet of stainless steel having a thickness of about 0.08 mm to about 0.1 mm. The leg segments preferably have a width at least about 40% greater than the width of the arms of the cells. For example, the arms may have a width of about 0.05 mm, with the leg segments having a width of about 0.075 mm. The machined sheet would be finally polished as well known in this art.

More specifically, each of the diamond-shaped cells 17 has four arms 19 of preferably equal length which are connected to one another at their ends to form a diamond which, in the expanded configuration, as illustrated in FIG. 1, has four interior 90° angles. The aforementioned major diamond cells 17 of the overall repeating pattern are formed by two adjacent arms of each cell 17, together with two pairs of interconnected leg segments 13. Following rolling or otherwise forming into tubular configuration, a spot-welding operation is carried out to connect the vertices A of each diamond cell 15 located along the top edge of the generally rectangularly-shaped piece of material 11 to the junction points between adjacent leg segments 13 that are located along the bottom edge, i.e. at the locations marked B. This diamond-within-a-diamond pattern allows for compression or crimping of the framework to a smaller dimension, e.g. about one-half of the height shown in FIG. 1, without any substantial change in axial length.

When the stent is machined from flat metal stock, the tubular framework configuration may first be formed and then compressed to create a smaller diameter tubular structure. The leg segments 13 in the zig-zag, axially extending legs are oriented so as to be at an angle to each other of between about 120° and 140° and preferably at an angle of between about 125° and 135°. In viewing the framework shown in FIG. 1, it can be seen that each leg segment 13 ends at a junction point where it is in connection with two arms 19 of a diamond-shaped cell and the next adjoining leg segment 13. As a result, there is good stabilizing support at these locations. At the other two vertices of each diamond cell 17 that are not at junctions between leg segments, there is no lateral support. As a result, when the open framework structure is subjected to crimping or compressing force, the diamond-shaped cells 17 collapse in a direction transverse to the axis, significantly reducing the circumference of the tubular structure.

Figure 5:
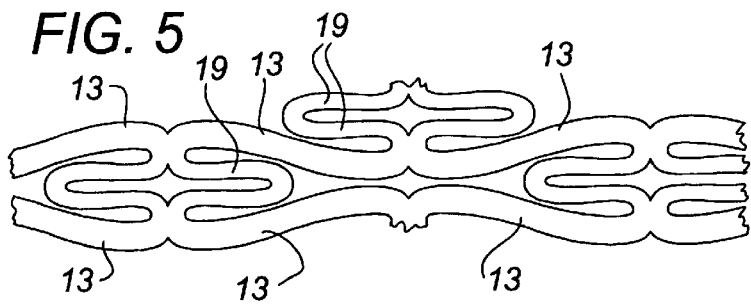
FIG. 5 is a fragmentary elevation view of the stent material illustrated in FIG. 1 shown in its crimped condition.

FIG. 5 is a fragmentary view of a stent made from the material 11 shown in its compressed condition, where it can be seen that the triangular cells 17 have completely collapsed. The arms 19 of the diamond cells 17 lie adjacent to each other in pairs. The zig-zag configuration of the legs has now reversed, i.e. compared to the orientation in the expanded configuration illustrated in FIG. 1, the orientation is the inverse of what it was. However, the leg segments 13 are still oriented at about the same angle to each other. The collapsing of the diamond-shaped cells 17 has no effect upon the axial length of the tubular structure because they are isolated from the legs, and there is no significant change in the axial length of the stent in its unexpanded and expanded configurations. However, a slight extension in length occurs during transition when the adjacent leg segments approach an angle of 180°.

Figure 2:
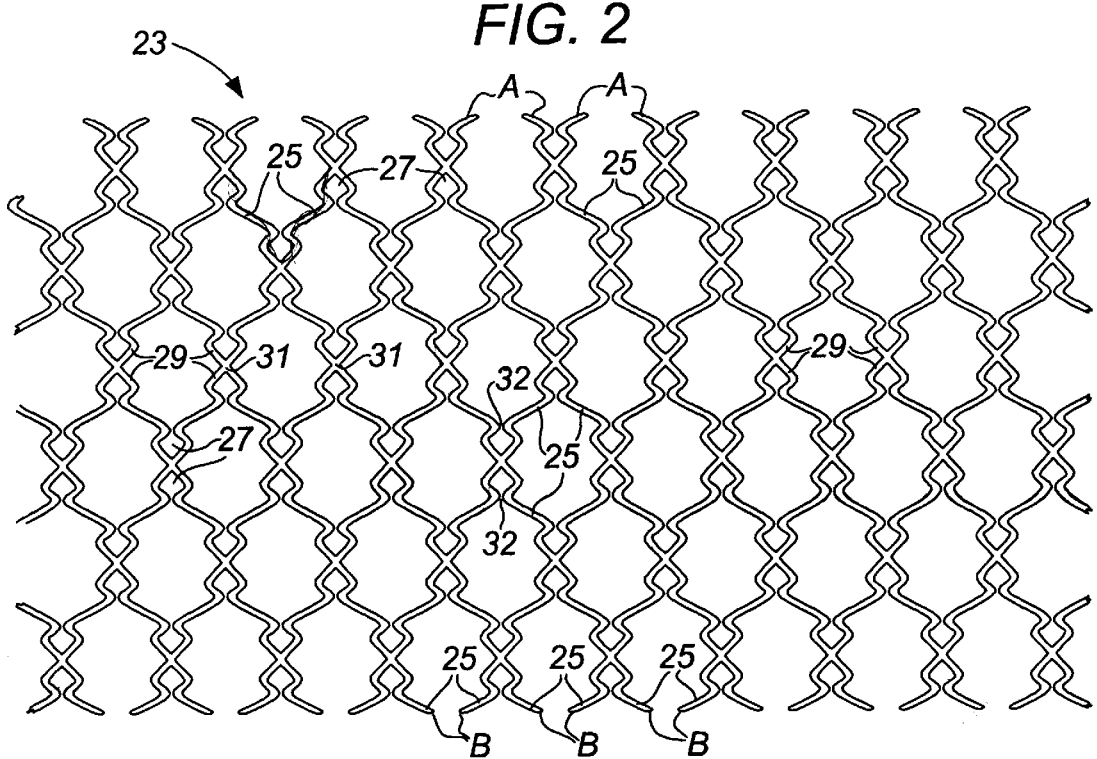
FIG. 2 is a view similar to FIG. 1 illustrating an alternative material design to that shown in FIG. 1 which alternative employs pairs of small diamond cells.

Illustrated in FIG. 2 is an alternative embodiment of a piece or blank of sheet material 23 similarly designed to be formed into an expandable intraluminal stent. The material also uses a type of general pattern of a diamond-in-a-diamond; however, in this repeating pattern, axially extending legs that are formed by short leg segments 25, are spaced apart not by single minor diamond cells, but by pairs of diamond cells 27 having a common vertex. The material 23 can likewise be made by machining from a single sheet. Alternatively, it could be formed from a plurality of individual wire sections, each of which would ultimately run circumferentially of the tubular stent. As depicted in FIG. 2, if such lengths of wire were used, adjacent, vertically oriented, formed lengths of wire would be joined, as by spot-welding, at three points. As indicated hereinbefore, the framework material is preferably machined from a unitary sheet or tube, and to achieve more efficient use of material, the structure is machined in the unexpanded form which also eliminates the step of crimping or compressing.

The open framework structure shown in FIG. 2 is such that each of the diamond cells of the interconnected pairs has a common vertex 31 and an opposite open vertex 32 which lies at what would otherwise be the junction between the ends of the adjacent leg segments 25. As a result, the leg segments 25, instead of being directly connected to one another at these junctions, are indirectly connected through the arms 29 of one of the diamond cells 27. Even though they are not directly interconnected, the leg segments 25 are still oriented at an angle to each other between about 120° and about 140° as mentioned above. Following rolling of the material 23 or otherwise forming it into a tubular configuration, spot welding or the like is carried out so as to join the ends of the arms 29 at each open vertex along the upper edge of the sheet, at the points marked A, by spot welding or the like, to the ends of the leg segments 25 at the points marked B.

Figure 3:
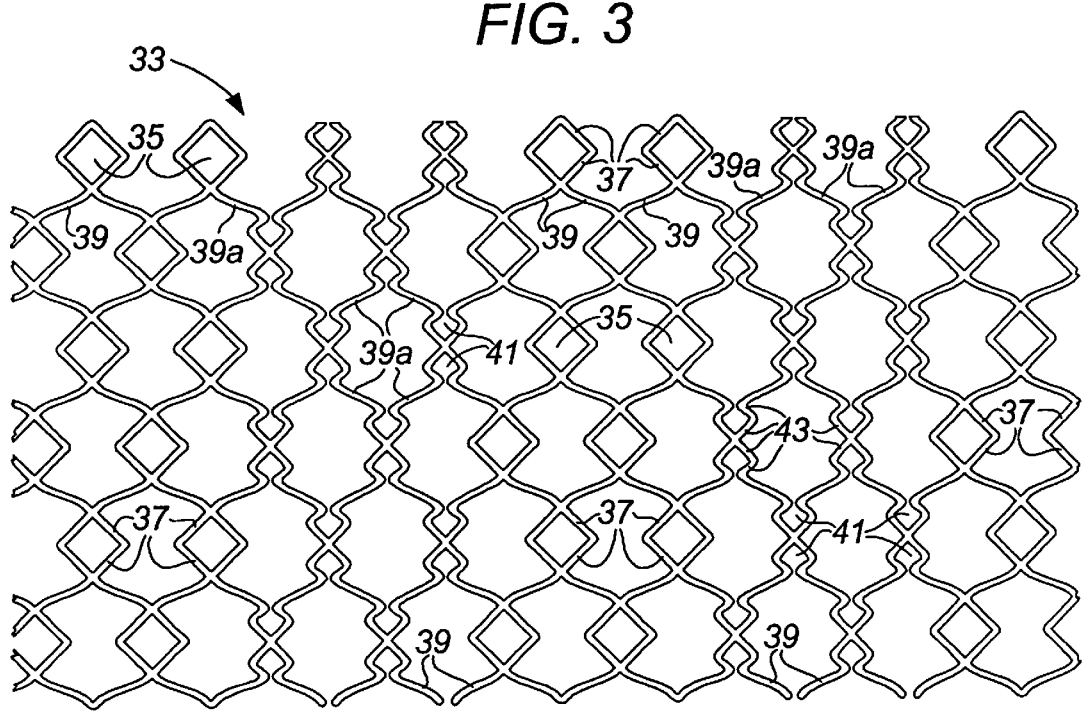
FIG. 3 shows a further alternative material design that constitutes a hybrid version of the two materials shown in FIGS. 1 and 2.

Illustrated in FIG. 3 is a further alternative embodiment of a piece or blank of sheet material 33, designed to be formed into an expandable intraluminal stent, having a structure which is a hybrid of those shown in FIGS. 1 and 2. The material 33 uses alternating sections of the FIG. 1 material and the FIG. 2 material. In a center section and the two lateral edge sections, larger diamond cells 35 are formed, similar to the cells 17. Each of these diamond cells 35 has four arms 37 of equal length, and the upper and lower vertices are located at junctions between adjacent interconnected leg segments or ribs 39. The two intermediate regions resemble the framework construction shown in FIG. 2. Pairs of smaller diamond cells 41 with a common vertex and four arms 43 of equal length indirectly interconnect leg segments 39a at the locations of the open vertices.

Figure 5A:
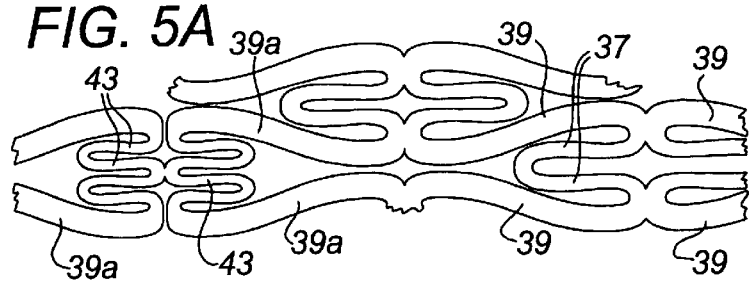
FIG. 5A is a fragmentary elevation view of the stent material illustrated in FIG. 3 shown in its crimped condition.

The blank 33 is used to form a stent as previously described by rolling or otherwise deforming it into a tubular form and then spot-welding or the like at the aligned points between the two common axially extending edges. After formation into such a tube, it is conventionally crimped as by being forced axially through a tubular passageway of ever-decreasing diameter to effect such a smooth transition from the expanded, highly open framework to a fairly closely compressed cylindrical form, such as that depicted in the fragmentary view FIG. 5A. The arms 37 which make up the larger diamond cells 35 lie generally adjacent one another in pairs. Likewise, the arms 43 of the smaller diamond cells 41 are similarly compressed so as to lie adjacent one another, as shown in the left-hand portion of FIG. 5A.

In the expanded material shown in FIG. 3, the leg segments 39 and 39a are oriented at an angle of between 125° to 135° to each other, which would be the "internal" angle in the major diamond pattern as described hereinbefore. During crimping, these two pairs of leg segments 39, 39a pass through an angle of orientation to each other of 180°. Following the completion of crimping, the same two leg segments are still oriented at about an angle of about 125° to about 135° to each other; however, now that angle is on the exterior of what was once the major diamond cell in the expanded configuration. What was once the internal angle is now the inverse of that angle. For example, if the interconnected leg segments in the major cells were oriented at an interior angle of about 130° to each other, that "interior" angle would now be about 230° in the crimped configuration, as can be seen in FIG. 5. However, because the relative angular orientation of the individual leg segments to one another is still the same, i.e. about 130°, in both the expanded and the unexpanded configurations of the stent, the axial length of the legs has not changed; thus, the length of the stent in its crimped condition is substantially the same as the length of the stent in its expanded configuration. It can of course be seen that the expansion/compression of the diamond cells 35 and 41 has no effect upon the axial length of the stent, whereas it provides the major amount of the circumferential dimensional change.

Figure 4:
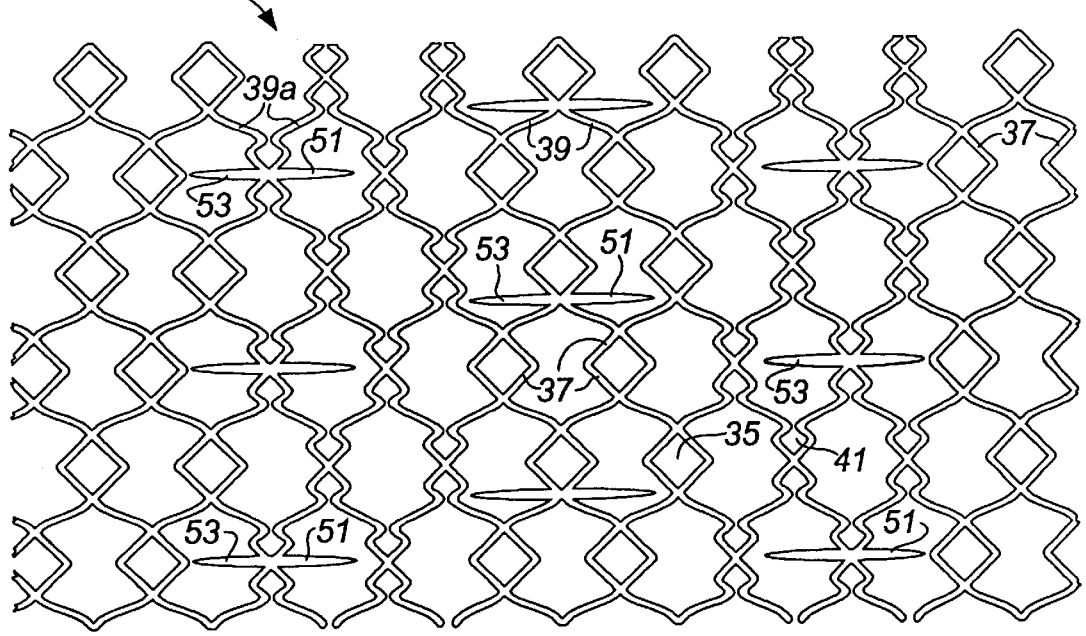
FIG. 4 is a view similar to FIG. 1 which is another alternative material design similar to that shown in FIG. 3 but which incorporates needle-like projections that extend in opposite longitudinal directions and that are employed to mount a tubular biological membrane exterior of the stent.

Shown in FIG. 4 is a piece or-blank of stent material 33' which is essentially the same construction as the material 33 with the exception that a plurality of pairs of oppositely extending needle-like projections or prongs 51 and 53 are included. These projections are located so they are encompassed within what has sometimes been termed the major diamond cells, and they are oriented axially, i.e. they will lie parallel to the longitudinal axis of the fabricated tubular stent body. The projections 51 and the projections 53 extend in opposite directions and are used to affix a tubular biological membrane to the stent so that such a membrane can be transported in surrounding relationship about a crimped stent to a desired location within a diseased artery or the like. Once so located and following radial expansion of the stent, this biomembrane will serve to provide a smooth interface between the diseased or torn (dissected) wall of the artery and the stent itself, thus isolating the major portion of the metal stent from the intima. In this form, the stent combination can simultaneously deal with two major and critical problems of coronary or other occlusive disease. Tubular biological membranes that are frequently employed as blood vessel substitutes are available from various sources, such as Shellhigh, Inc. of Millbourne, N.J., USA; they are typically given a tissue preservation treatment, such that as offered by Shellhigh as its No-React™ treatment. Such treatments are commonly known in this art and may be employed to "fix" the tissue, i.e. to cross-link the collagenaceous chains of the tissue to give it increased strength, and also to endow the tissue with some resistance to calcification. Mammary and other blood vessels from animals of the bovine and porcine species, for example, are available and frequently employed for such blood vessel substitutes; they will serve as suitable biomembranes for the present invention. There may be advantages in affixing the untreated blood vessels following harvesting, and then treating the blood vessel as it has a tendency to shrink during fixation. This will cause the treated vessel to lie close to the surface of the stent within the catheter sheath; however, such biological membrane will stretch along with the expansion of the stent without tearing. In addition to the aforementioned stabilizing treatments, these biomembranes may be used to carry and deliver different classes of medications from the interior and the exterior surfaces. For example, the intima may be medicated by impregnating the exterior surface with an antiproliferative medication, such as is well known in this art, which would serve to avoid rapid growth of the adjacent tissue of the living blood vessel in which the stent-biomembrane combination is being placed. At the same time, the interior surface of the biomembrane might be impregnated with pharmaeuticals that are released slowly into the bloodstream; examples include antithrombotic agents, such as heparin and salicilates, thrombolytic drugs, such as TPA, SK (streptokinase) and Reopro™, and slow-releasing gene therapy molecules which stimulate rebuilding of new blood vessels, i.e. neovascular proliferation.

Figure 6:
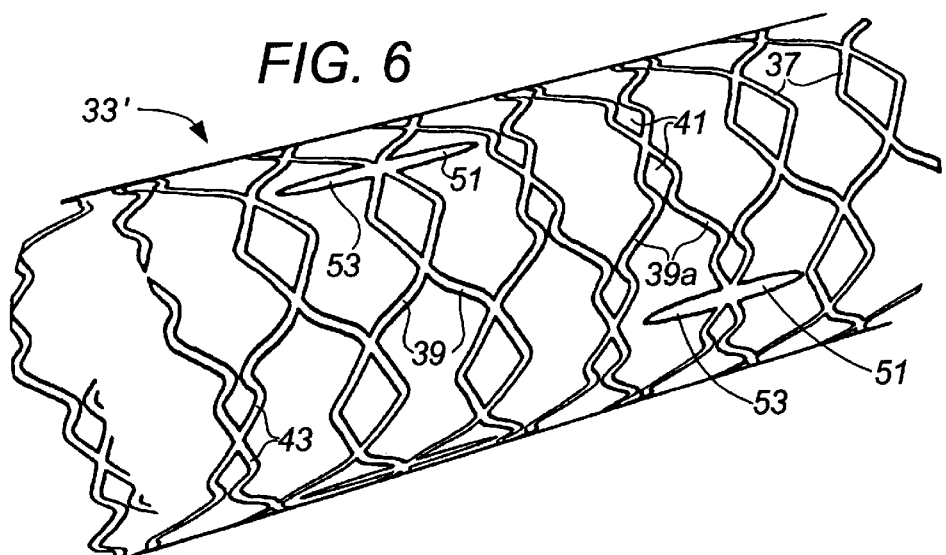
FIG. 6 is a perspective view of a tubular stent made from the material of FIG. 4 shown in its expanded configuration.

Illustrated in FIG. 6 is a fragmentary perspective view of a stent fabricated from the material illustrated in FIG. 4. In this tubular configuration, the prongs 57, 53 are oriented axially of the tubular open framework so that the distance between the adjacent prongs does not change as a result of expansion/compression of the stent. FIG. 6 of course illustrates the stent in its expanded configuration which would occur within the blood vessel, and the tubular biomembrane would be installed about the stent when it is in its compressed or unexpanded condition as explained hereinafter.

Figure 7:
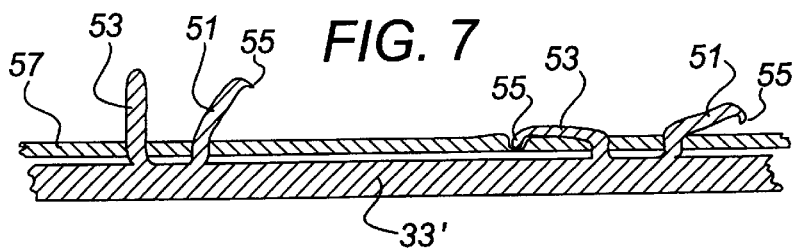
FIG. 7 is a fragmentary sectional view through a crimped tubular stent made from material shown in FIG. 4 with a tubular membrane mounted in place and in the process of being staked thereupon, with the radially outwardly bent needle-like prongs being shown as they are in various stages of being bent back toward the plane of the stent.
Figure 8:
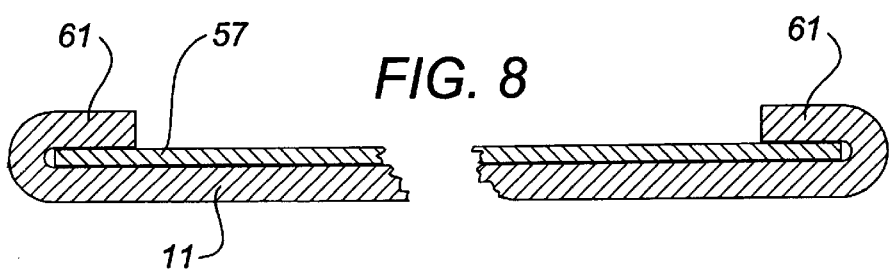
FIG. 8 is a sectional view similar to FIG. 7 showing an alternative method of joining a tubular membrane to a crimped stent by folding each end of the tubular stent back upon itself to securely sandwich the ends of the tubular membrane therebetween.

Illustrated in FIG. 7 a fragmentary sectional view of a crimped tubular stent made from the material 33' which shows a biological membrane 57' that is punctured by the pairs of needle-like prongs 51, 53 which are bent radially outward for the installation of the biomembrane. The biomembrane 57 is installed over these radially oriented projections and aligned so that there is generally no slack in the membrane longitudinally. There could be shallow folds of membrane between axial rows of pairs of prongs, or the biomembrane could have shrunk to a diameter close to that of the compressed stent. Precise radial cuts are preferably made in the tubular membrane at the sites where the prongs will penetrate the membrane so there will be no local tearing. Once the membrane is in place, the tips of the projections 51 and 53 may optionally be bent in the appropriate directions to create short tangs 55, as shown on three of the four projections in FIG. 6. The prongs 51 are then bent to the right, as shown in two different stages, until they again lie essentially in the plane of the tubular stent. The projections 53, with their tips bent in the opposite direction to form tangs 55, are then bent to the left to the orientation as shown in one instance so as to firmly secure the biological membrane 57 to the stent with the tangs embedded in the surface. Thereafter, upon circumferential expansion of the tubular stent within the blood vessel of a patient, the biological membrane becomes spread out and/or stretches tautly on the exterior surface of the expanded stent with no folds or wrinkles because of the fact that the axial length of the stent does not shorten during its transition to the expanded condition, having substantially the same length as in the crimped configuration. Such biological membranes have considerable stretchability, as mentioned hereinbefore, so the slight axial expansion that occurs when the leg segments pass through an angular orientation of 180° during expansion creates no difficulty.

Illustrated in FIG. 7 is an alternative method of joining a tubular biological membrane 57 to a stent which can be effectively carried out using stent material that does not become foreshortened upon expansion. The stent material, for example, can be any of the constructions shown in FIGS. 1, 2 or 3. The stent material is formed into its tubular condition, and then the tubular biological membrane is installed in place regularly surrounding the stent which is in the compressed configuration, with the tubular membrane 57 being slightly shorter than the stent so as to leave a short margin at each axial end. Each end 61 of the stent is first flared outward and then folded back upon itself so as to sandwich each end of the tubular membrane 57 between two layers of stent material. Because of the relatively open pattern at each end of the stent, each end of the tubular membrane 57 becomes well secured by this folding and crimping of the malleable metal stent material at spaced apart locations which might lie between shallow folds in the membrane. Thus, the biological membrane 57 can be effectively carried in place as part of such a stent combination, and upon expansion of the stent by an interior balloon catheter or the like, it provides a tubular support structure with a biological membrane smoothly disposed about its entire exterior circumference.

Although the invention has been described in terms of its preferred embodiments which constitute the best mode presently envisioned by the inventor for carrying out the invention, it should be understood that various changes and modifications as would be obvious to one having ordinary skill in this art, may be made without departing from the scope of the invention which is defined by the appended claims. In this respect, whereas the materials from which the stents are preferably constructed are primarily illustrated in their expanded conditions, it should be understood that they may be laser-cut or otherwise suitably machined from malleable sheet or tube material in their compressed or unexpanded condition and suitably polished in this configuration to render them ready for installation in a human body. Moreover, it may be preferable to machine them from a tube of intermediate diameter and polish the tubular stent in such a partially expanded state prior to crimping. The medications with which such biological membrane may be impregnated may be designed for fairly immediate release, or for slow release over a predetermined period of time, and different classes of medications can be carried by the interior and the exterior of a biological membrane in the form of a mammalian blood vessel. Whereas the exterior surface may be impregnated with well known anti-proliferative compounds to prevent local intimal proliferation, the interior surface may be impregnated with thrombolytic agents, such as TPA, SK and urokinase, or with antithrombotic agents, such as heparin and salicitates, or with gene therapy molecules designed to promote neovascularization.

Particular features of the invention are emphasized in the claims which follow.

What is claimed is:

1. An unexpanded intraluminal stent which is radially expandable to an operative configuration in which it provides interior support for a blood vessel, which stent comprises a tubular structure capable of being radially expanded from a smaller diameter unexpanded configuration to a larger diameter fully expanded configuration without substantially any shortening of its axial length, said structure being formed of a malleable material which in its fully expanded configuration will effectively resist return to a smaller diameter condition when subject to normal forces acting within the body of a mammal, said structure constituting an open framework which includes a plurality of axially extending leg means that extend from one axial end to the other of said tubular structure, said leg means each including a plurality of leg segments which are interconnected with one another in the fully expanded configuration at an angle of between about 120° and 140° in a zig-zag pattern, and said legs being spaced apart from one another in the fully expanded configuration by a plurality of open diamond-shaped cells which are axially unconnected to one another, at least one vertex of each of said diamond-shaped cells being connected to at least one of said legs, wherein the leg do not form part of the diamond-shaped cells.

2. The stent according to claim 1 wherein said adjacent leg segments are oriented at an angle of between about 125° and about 135° to each other both in said unexpanded configuration and in said expanded configuration.

3. The stent according to claim 1 wherein each of said cells includes four arms having approximately the same length and width as one another.

4. The stent according to claim 3 wherein the width of said leg segments is at least about 40% greater than the width of said arms.

5. An unexpanded intraluminal stent which is radially expandable to an operative configuration in which it provides interior support for a blood vessel, which stent comprises a tubular structure capable of being radially expanded from a smaller diameter unexpanded configuration to a larger diameter fully expanded configuration without any substantial shortening of its axial length, said structure being formed of a malleable material which in its fully expanded configuration will effectively resist return to a smaller diameter condition when subject to normal forces acting within the body of a mammal, said structure constituting an open framework which includes a plurality of axially extending leg means that extend from one axial end to the other of said tubular structure, said leg means each including a plurality of leg segments which are interconnected with one another in the fully expanded configuration at an angle of between about 120° and 140° in a zig-zag pattern, and said legs being spaced apart from one another in the fully expanded configuration by a plurality of spacers which include open diamond-shaped cells that are connected at one vertex to at least one of said legs and unconnected to one another in an axial direction, and said spacers each comprising a pair of diamond-shaped cells which each have four arms and a common vertex, said pair being aligned transverse to the axis of said tubular structure.

6. The stent according to claim 5 wherein said arms all have about the same length.

7. The stent according to claim 6 wherein the width of said leg segments is at least about 40% greater than the width of said arms.

8. The stent according to claim 5 wherein each of said adjacent leg segments is joined at its end to the end of one of said arms of said cells and is spaced apart from the end of said adjacent leg segment.

9. An unexpanded intraluminal stent which is radially expandable to an operative configuration in which it provides interior support for a blood vessel, which stent comprises a tubular structure capable of being radially expanded from a smaller diameter unexpanded configuration to a larger diameter fully expanded configuration without substantially shortening its axial length, said structure being formed of a malleable material which in its expanded configuration will effectively resist return to a smaller diameter condition when subject to normal forces acting within the body of a mammal, said structure being an open unitary framework which includes a plurality of axially extending legs which extend from axial end to the other end of said tubular structure, and a plurality of open diamond-shaped cells connected at vertices to said adjacent legs, which cells are unconnected to one another in an axial direction, wherein the legs do not form part of the diamond-shaped cells.

10. The stent of claim 9 wherein said legs comprise a plurality of leg segments which are directly joined end-to-end so that each leg constitutes a continuous zig-zag line.

11. The stent of claim 9 wherein each said leg segment terminates in a unitary junction to an adjacent leg segment and to one vertex of one of said diamond cells.

12. The stent of claim 11 wherein each said junction joins two said leg segments and two arms which constitute one-half of one of said diamond-shaped cells, with said leg segments having a width at least about 40% greater than said arms.

13. The stent of claim 12 wherein the opposite end of each of said arms to that which is joined at each said junction is connected only to another arm of said diamond-shaped cell so that, when said stent is transformed between its unexpanded and its expanded configurations, said two connected arms are bent from a generally parallel orientation to a generally perpendicular orientation.

14. The stent of claim 13 wherein the angular orientation of said adjacent leg segments is between about 120° and about 140° in both the expanded and unexpanded configurations.

15. The combination of the stent of claim 12 and a tubular biological membrane in the form of a mammalian blood vessel segment wherein said tubular structure includes a plurality of prongs which are connected to various of said junctions and aligned axially in regions between adjacent legs and which prongs can be bent to a generally radial orientation to permit the attachment of said blood vessel segment in surrounding relationship, said prongs protruding through said blood vessel segment wall and being aligned in an axial orientation to secure said blood vessel segment thereto.

* * * * *